(12) United States Patent
Lopez-Fraga et al.

(10) Patent No.: US 9,018,183 B2
(45) Date of Patent: Apr. 28, 2015

(54) SIRNA AND THEIR USE IN METHODS AND COMPOSITIONS FOR THE TREATMENT AND/OR PREVENTION OF EYE CONDITIONS

(75) Inventors: Marta Lopez-Fraga, Madrid (ES); Ana Isabel Jimenez, Madrid (ES); Tamara Martinez Valcarel, Madrid (ES)

(73) Assignee: Sylentis S.A.U., Madrid (ES)

(*) Notice: Subject to any disclaimer, the term of this patent is extended or adjusted under 35 U.S.C. 154(b) by 0 days.

(21) Appl. No.: 13/699,958

(22) PCT Filed: May 27, 2011

(86) PCT No.: PCT/GB2011/051007
§ 371 (c)(1),
(2), (4) Date: Nov. 26, 2012

(87) PCT Pub. No.: WO2011/148193
PCT Pub. Date: Dec. 1, 2011

(65) Prior Publication Data
US 2013/0079389 A1 Mar. 28, 2013

(30) Foreign Application Priority Data
May 27, 2010 (EP) .................................... 10380074

(51) Int. Cl.
*C12N 15/11* (2006.01)
*C07H 21/02* (2006.01)
*A61K 31/713* (2006.01)
*C12N 15/113* (2010.01)

(52) U.S. Cl.
CPC ............. *C07H 21/02* (2013.01); *A61K 31/713* (2013.01); *C12N 15/1138* (2013.01); *C12N 2310/14* (2013.01); *C12N 2310/321* (2013.01)

(58) Field of Classification Search
USPC ........................................................ 514/44 A
See application file for complete search history.

(56) References Cited

U.S. PATENT DOCUMENTS

| 8,354,385 B2 * | 1/2013 | Boj et al. ................ 514/44 A |
| 2006/0122136 A1 | 6/2006 | Schubert et al. |
| 2008/0085998 A1 | 4/2008 | Khvorova et al. |
| 2010/0286230 A1 * | 11/2010 | Acosta Boj et al. ........ 514/44 A |

FOREIGN PATENT DOCUMENTS

| WO | WO 2007/045930 | 4/2007 |
| WO | WO 2009/023025 | 2/2009 |

OTHER PUBLICATIONS

Byrne et al. J. Ocular Pharmacology and Therapeutics 29:2013, pp. 855-864.*
Doench et al., "Specificity of microRNA Target Selection in Translational Repression," Genes Dev., 18:504-511, 2004.
Luna et al., "TRPV1 siRNA Topical Treatment Reduces the Response to Ocular Surface Irritation with Capsaicin," Invest. Ophthalmol. Vis. Sci., 48, E-Abstract and Poster, 373, 2007, 3 pages.
Gonzalez et al., "A New Treatment for Ocular Pain Associated to Dry Eye Syndrome Based on RNAi Technology: In Vivo Results," Invest. Ophthalmol. Vis. Sci., E-Abstract and Poster 4676, 2009, 3 pages.
Czauderna et al., "Structural Variations and Stabilising Modifications of Synthetic siRNAs in Mammalian Cells," Nucleic Acids Research, vol. 31, No. 11, pp. 2705-2716, Jun. 1, 2003.

* cited by examiner

*Primary Examiner* — Brian Whiteman
(74) *Attorney, Agent, or Firm* — Margaret B. Brivanlou; Leslie A. Serunian; King & Spalding LLP

(57) ABSTRACT

The invention relates to methods and compositions for the treatment/and or prevention of eye conditions related to high levels of expression and/or activity of the vanilloid-1 receptor (TRPV).

14 Claims, 3 Drawing Sheets ns of pain, neurogenic inflammation, and sometimes, in smooth muscle contraction and cough. As a matter of fact, recent evidence suggests a role of TRPV1 in

SEQUENCE LISTING

```
<160> NUMBER OF SEQ ID NOS: 41

<210> SEQ ID NO 1
<211> LENGTH: 19
<212> TYPE: DNA
<213> ORGANISM: Homo sapiens

<400> SEQUENCE: 1
aagcgcatct tctacttca                                               19

<210> SEQ ID NO 2
<211> LENGTH: 19
<212> TYPE: RNA
<213> ORGANISM: Artificial
<220> FEATURE:
<223> OTHER INFORMATION: siRNA against TRPV1

<400> SEQUENCE: 2
aagcgcaucu ucuacuuca                                               19

<210> SEQ ID NO 3
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: uracil has a 2'-O methyl group
<220> FEATURE:
<221> NAME/KEY: misc_feature
<222> LOCATION: (10)..(11)
<223> OTHER INFORMATION: uracil has a 2'-O methyl group
<220> FEATURE:
<221> NAME/KEY: misc_feature
<222> LOCATION: (16)..(17)
<223> OTHER INFORMATION: uracil has a 2'-O methyl group

<400> SEQUENCE: 3
```
aagcgcaucu ucuacuuca                                               19

<210> SEQ ID NO 4
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (1)..(2)
<223> OTHER INFORMATION: adenine has a 2'-O methyl group
<220> FEATURE:
<221> NAME/KEY: misc_feature
<222> LOCATION: (7)..(7)
<223> OTHER INFORMATION: adenine has a 2'-O methyl group
<220> FEATURE:
<221> NAME/KEY: misc_feature
<222> LOCATION: (14)..(14)
<223> OTHER INFORMATION: adenine has a 2'-O methyl group
<220> FEATURE:
<221> NAME/KEY: misc_feature
<222> LOCATION: (19)..(19)
<223> OTHER INFORMATION: adenine has a 2'-O methyl group

<400> SEQUENCE: 4
aagcgcaucu ucuacuuca                                               19

<210> SEQ ID NO 5
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (10)..(11)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (16)..(17)
<223> OTHER INFORMATION: n=deoxythymidine

<400> SEQUENCE: 5
aagcgcancn ncnacnnca                                               19

<210> SEQ ID NO 6
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (10)..(11)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:

```
<221> NAME/KEY: misc_feature
<222> LOCATION: (16)..(17)
<223> OTHER INFORMATION: n= deoxythymidine

<400> SEQUENCE: 6
aagcgcancn ncnacnnca                                                 19

<210> SEQ ID NO 7
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (20)..(21)
<223> OTHER INFORMATION: n=deoxythymidine

<400> SEQUENCE: 7
ucgccacgac augcucuugn n                                              21

<210> SEQ ID NO 8
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: uracil has a 2'-O methyl group
<220> FEATURE:
<221> NAME/KEY: misc_feature
<222> LOCATION: (13)..(13)
<223> OTHER INFORMATION: uracil has a 2'-O methyl group
<220> FEATURE:
<221> NAME/KEY: misc_feature
<222> LOCATION: (17)..(17)
<223> OTHER INFORMATION: uracil has a 2'-O methyl group

<400> SEQUENCE: 8
aagcgcaucu ucuacuuca                                                 19

<210> SEQ ID NO 9
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: uracil has a 2'-O methyl group
<220> FEATURE:
<221> NAME/KEY: misc_feature
<222> LOCATION: (17)..(17)
<223> OTHER INFORMATION: uracil has a 2'-O methyl group

<400> SEQUENCE: 9
aagcgcaucu ucuacuuca                                                 19

<210> SEQ ID NO 10
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (2)..(2)
<223> OTHER INFORMATION: adenine has a 2'-O methyl group
```

-continued

<220> FEATURE:
<221> NAME/KEY: misc_feature
<222> LOCATION: (7)..(7)
<223> OTHER INFORMATION: adenine has a 2'-O methyl group
<220> FEATURE:
<221> NAME/KEY: misc_feature
<222> LOCATION: (19)..(19)
<223> OTHER INFORMATION: adenine has a 2'-O methyl group

<400> SEQUENCE: 10
aagcgcaucu ucuacuuca                                                 19

<210> SEQ ID NO 11
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (2)..(2)
<223> OTHER INFORMATION: adenine has a 2'-O methyl group
<220> FEATURE:
<221> NAME/KEY: misc_feature
<222> LOCATION: (19)..(19)
<223> OTHER INFORMATION: adenine has a 2'-O methyl group

<400> SEQUENCE: 11
aagcgcaucu ucuacuuca                                                 19

<210> SEQ ID NO 12
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (11)..(11)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (16)..(17)
<223> OTHER INFORMATION: n=deoxythymidine

<400> SEQUENCE: 12
aagcgcancu ncnacnnca                                                 19

<210> SEQ ID NO 13
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (11)..(11)
<223> OTHER INFORMATION: n=deoxythymidine
<220> FEATURE:
<221> NAME/KEY: misc_feature
<222> LOCATION: (13)..(13)

```
<223> OTHER INFORMATION: n=deoxythymidine
<220> FEATURE:
<221> NAME/KEY: misc_feature
<222> LOCATION: (17)..(17)
<223> OTHER INFORMATION: n=deoxythymidine

<400> SEQUENCE: 13
aagcgcancu ncnacunca                                                    19

<210> SEQ ID NO 14
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (17)..(17)
<223> OTHER INFORMATION: n=deoxythymidine

<400> SEQUENCE: 14
aagcgcancu ucnacunca                                                    19

<210> SEQ ID NO 15
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (17)..(17)
<223> OTHER INFORMATION: n=deoxythymidine

<400> SEQUENCE: 15
aagcgcancu ucuacunca                                                    19

<210> SEQ ID NO 16
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (8)..(8)
<223> OTHER INFORMATION: n=deoxythymidine
<220> FEATURE:
<221> NAME/KEY: misc_feature
<222> LOCATION: (17)..(17)
<223> OTHER INFORMATION: n=deoxythymidine

<400> SEQUENCE: 16
aagcgcancu ucuacunca                                                    19

<210> SEQ ID NO 17
<211> LENGTH: 19
<212> TYPE: RNA
<213> ORGANISM: Artificial
```

```
<220> FEATURE:
<223> OTHER INFORMATION: siRNA against TRPV1

<400> SEQUENCE: 17
cgcaucuucu acuucaacu                                              19

<210> SEQ ID NO 18
<211> LENGTH: 19
<212> TYPE: RNA
<213> ORGANISM: Artificial
<220> FEATURE:
<223> OTHER INFORMATION: siRNA against TRPV1

<400> SEQUENCE: 18
gcgcaucuuc uacuucaac                                              19

<210> SEQ ID NO 19
<211> LENGTH: 19
<212> TYPE: RNA
<213> ORGANISM: Artificial
<220> FEATURE:
<223> OTHER INFORMATION: siRNA against TRPV1

<400> SEQUENCE: 19
aaagccaugc ucaaccugc                                              19

<210> SEQ ID NO 20
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (20)..(21)
<223> OTHER INFORMATION: n=deoxythymidine

<400> SEQUENCE: 20
ugaucgcagg aguaucuuun n                                           21

<210> SEQ ID NO 21
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (20)..(21)
<223> OTHER INFORMATION: n=deoxythymidine

<400> SEQUENCE: 21
caagaucgca caggagagcn n                                           21

<210> SEQ ID NO 22
<211> LENGTH: 19
<212> TYPE: RNA
<213> ORGANISM: Artificial
<220> FEATURE:
<223> OTHER INFORMATION: siRNA against TRPV1

<400> SEQUENCE: 22
ugaaguagaa gaugcgcuu                                              19

<210> SEQ ID NO 23
<211> LENGTH: 19
<212> TYPE: RNA
```

```
<213> ORGANISM: Artificial
<220> FEATURE:
<223> OTHER INFORMATION: siRNA against TRPV1

<400> SEQUENCE: 23
ugaaguagaa gaugcgcuu                                                        19

<210> SEQ ID NO 24
<211> LENGTH: 19
<212> TYPE: RNA
<213> ORGANISM: Artificial
<220> FEATURE:
<223> OTHER INFORMATION: siRNA against TRPV1

<400> SEQUENCE: 24
ugaaguagaa gaugcgcuu                                                        19

<210> SEQ ID NO 25
<211> LENGTH: 19
<212> TYPE: RNA
<213> ORGANISM: Artificial
<220> FEATURE:
<223> OTHER INFORMATION: siRNA against TRPV1

<400> SEQUENCE: 25
ugaaguagaa gaugcgcuu                                                        19

<210> SEQ ID NO 26
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (1)..(1)
<223> OTHER INFORMATION: n=deoxythymidine
<220> FEATURE:
<221> NAME/KEY: misc_feature
<222> LOCATION: (6)..(6)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine
<220> FEATURE:
<221> NAME/KEY: misc_feature
<222> LOCATION: (18)..(19)
<223> OTHER INFORMATION: n=deoxythymidine

<400> SEQUENCE: 26
ngaagnagaa gangcgcnn                                                        19

<210> SEQ ID NO 27
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (20)..(21)
<223> OTHER INFORMATION: n=deoxythymidine

<400> SEQUENCE: 27
caagagcaug ucguggcgan n                                                     21

<210> SEQ ID NO 28
<211> LENGTH: 19
```

```
<212> TYPE: RNA
<213> ORGANISM: Artificial
<220> FEATURE:
<223> OTHER INFORMATION: siRNA against TRPV1

<400> SEQUENCE: 28
ugaaguagaa gaugcgcuu                                                    19

<210> SEQ ID NO 29
<211> LENGTH: 19
<212> TYPE: RNA
<213> ORGANISM: Artificial
<220> FEATURE:
<223> OTHER INFORMATION: siRNA against TRPV1

<400> SEQUENCE: 29
ugaaguagaa gaugcgcuu                                                    19

<210> SEQ ID NO 30
<211> LENGTH: 19
<212> TYPE: RNA
<213> ORGANISM: Artificial
<220> FEATURE:
<223> OTHER INFORMATION: siRNA against TRPV1

<400> SEQUENCE: 30
ugaaguagaa gaugcgcuu                                                    19

<210> SEQ ID NO 31
<211> LENGTH: 19
<212> TYPE: RNA
<213> ORGANISM: Artificial
<220> FEATURE:
<223> OTHER INFORMATION: siRNA against TRPV1

<400> SEQUENCE: 31
ugaaguagaa gaugcgcuu                                                    19

<210> SEQ ID NO 32
<211> LENGTH: 19
<212> TYPE: RNA
<213> ORGANISM: Artificial
<220> FEATURE:
<223> OTHER INFORMATION: siRNA against TRPV1

<400> SEQUENCE: 32
ugaaguagaa gaugcgcuu                                                    19

<210> SEQ ID NO 33
<211> LENGTH: 19
<212> TYPE: RNA
<213> ORGANISM: Artificial
<220> FEATURE:
<223> OTHER INFORMATION: siRNA against TRPV1

<400> SEQUENCE: 33
ugaaguagaa gaugcgcuu                                                    19

<210> SEQ ID NO 34
<211> LENGTH: 19
<212> TYPE: RNA
<213> ORGANISM: Artificial
<220> FEATURE:
<223> OTHER INFORMATION: siRNA against TRPV1

<400> SEQUENCE: 34
```
ugaaguagaa gaugcgcuu                                                  19

<210> SEQ ID NO 35
<211> LENGTH: 19
<212> TYPE: RNA
<213> ORGANISM: Artificial
<220> FEATURE:
<223> OTHER INFORMATION: siRNA against TRPV1

<400> SEQUENCE: 35
ugaaguagaa gaugcgcuu                                                  19

<210> SEQ ID NO 36
<211> LENGTH: 19
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (6)..(6)
<223> OTHER INFORMATION: n=deoxythymidine
<220> FEATURE:
<221> NAME/KEY: misc_feature
<222> LOCATION: (13)..(13)
<223> OTHER INFORMATION: n=deoxythymidine

<400> SEQUENCE: 36
ugaagnagaa gangcgcuu                                                  19

<210> SEQ ID NO 37
<211> LENGTH: 19
<212> TYPE: RNA
<213> ORGANISM: Artificial
<220> FEATURE:
<223> OTHER INFORMATION: siRNA against TRPV1

<400> SEQUENCE: 37
aguugaagua gaagaugcg                                                  19

<210> SEQ ID NO 38
<211> LENGTH: 19
<212> TYPE: RNA
<213> ORGANISM: Artificial
<220> FEATURE:
<223> OTHER INFORMATION: siRNA against TRPV1

<400> SEQUENCE: 38
guugaaguag aagaugcgc                                                  19

<210> SEQ ID NO 39
<211> LENGTH: 19
<212> TYPE: RNA
<213> ORGANISM: Artificial
<220> FEATURE:
<223> OTHER INFORMATION: siRNA against TRPV1

<400> SEQUENCE: 39
gcagguugag cauggcuuu                                                  19

<210> SEQ ID NO 40
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature

```
<222> LOCATION: (20)..(21)
<223> OTHER INFORMATION: n=deoxythymidine

<400> SEQUENCE: 40
aaagauacuc cugcgaucan n                                              21

<210> SEQ ID NO 41
<211> LENGTH: 21
<212> TYPE: RNA
<213> ORGANISM: Artificial
<220> FEATURE:
<223> OTHER INFORMATION: siRNA against TRPV1
<220> FEATURE:
<221> NAME/KEY: misc_feature
<222> LOCATION: (20)..(21)
<223> OTHER INFORMATION: n=deoxythymidine

<400> SEQUENCE: 41
gcucuccugu gcgaucuugn n                                              21
```

SIRNA AND THEIR USE IN METHODS AND COMPOSITIONS FOR THE TREATMENT AND/OR PREVENTION OF EYE CONDITIONS

FIELD OF THE INVENTION

The present invention relates to the provision of siRNA products and their use in methods and compositions for the treatment and/or prevention of eye conditions related to high levels of expression and or activity of the transient receptor potential vanilloid (TRPV1) using RNA interference. Amongst others, eye conditions associated to ocular pain such as discomfort and altered sensitivity of the cornea following refractive surgery, use of contact lenses, dry eye syndrome, and Sjogren's syndrome, are to be mitigated.

BACKGROUND OF THE INVENTION

RNA interference (RNAi) is a naturally occurring regulatory mechanism of most eukaryotic cells that uses small double stranded RNA (dsRNA) molecules to direct homology-dependent gene silencing. Its discovery by Fire and Mello in the worm *C. elegans* {Fire, 1998} was awarded the Nobel prize in 2006. Shortly after its first description, RNAi was also shown to occur in mammalian cells, not through long dsRNAs but by means of double-stranded small interfering RNAs (siRNAs) 21 nucleotides long {Elbashir, 2001}.

The process of RNA interference is thought to be an evolutionarily-conserved cellular defense mechanism used to prevent the expression of foreign genes and is commonly shared by diverse phyla and flora, where it is called post-transcriptional gene silencing. Since the discovery of RNAi mechanism there has been an explosion of research to uncover new compounds that can selectively alter gene expression as a new way to treat human disease by addressing targets that are otherwise "undruggable" with traditional pharmaceutical approaches involving small molecules or proteins.

According to current knowledge, the mechanism of RNAi is initiated when long double stranded RNAs are processed by an RNase III-like protein known as Dicer. The protein Dicer typically contains an N-terminal RNA helicase domain, an RNA-binding so-called Piwi/Argonaute/Zwille (PAZ) domain, two RNase III domains and a double-stranded RNA binding domain (dsRBD) {Collins, 2005} and its activity leads to the processing of the long double stranded RNAs into 21-24 nucleotide double stranded siRNAs with 2 base 3' overhangs and a 5' phosphate and 3' hydroxyl group. The resulting siRNA duplexes are then incorporated into the effector complex known as RNA-induced silencing complex (RISC), where the antisense or guide strand of the siRNA guides RISC to recognize and cleave target mRNA sequences {Elbashir, 2001} upon adenosine-triphosphate (ATP)-dependent unwinding of the double-stranded siRNA molecule through an RNA helicase activity {Nykanen, 2001}. The catalytic activity of RISC, which leads to mRNA degradation, is mediated by the endonuclease Argonaute 2 (AGO2) {Liu, 2004; Song, 2004}. AGO2 belongs to the highly conserved Argonaute family of proteins. Argonaute proteins are ~100 KDa highly basic proteins that contain two common domains, namely PIWI and PAZ domains {Cerutti, 2000}. The PIWI domain is crucial for the interaction with Dicer and contains the nuclease activity responsible for the cleavage of mRNAs {Song, 2004}. AGO2 uses one strand of the siRNA duplex as a guide to find messenger RNAs containing complementary sequences and cleaves the phosphodiester backbone between bases 10 and 11 relative to the guide strand's 5' end {Elbashir, 2001}. An important step during the activation of RISC is the cleavage of the sense or passenger strand by AGO2, removing this strand from the complex {Rand, 2005}. Crystallography studies analyzing the interaction between the siRNA guide strand and the PIWI domain reveal that it is only nucleotides 2 to 8 that constitute a "seed sequence" that directs target mRNA recognition by RISC, and that a mismatch of a single nucleotide in this sequence may drastically affect silencing capability of the molecule {Ma, 2005; Doench 2004; Lewis, 2003}. Once the mRNA has been cleaved, and due to the presence of unprotected RNA ends in the fragments, the mRNA is further cleaved and degraded by intracellular nucleases and will no longer be translated into proteins {Orban, 2005} while RISC will be recycled for subsequent rounds {Hutvagner, 2002}. This constitutes a catalytic process leading to the selective reduction of specific mRNA molecules and the corresponding proteins. It is possible to exploit this native mechanism for gene silencing with the purpose of regulating any gene(s) of choice by directly delivering siRNA effectors into the cells or tissues, where they will activate RISC and produce a potent and specific silencing of the targeted mRNA.

Many studies have been published describing the ideal features a siRNA should have to achieve maximum effectiveness, regarding length, structure, chemical composition, and sequence. Initial parameters for siRNA design were set out by Tuschl and co-workers in WO02/44321, although many subsequent studies, algorithms and/or improvements have been published since then.

Also, a lot of effort has been put into enhancing siRNA stability as this is perceived as one of the main obstacles for therapy based on siRNA, given the ubiquitous nature of RNAses in biological fluids. One of the main strategies followed for stability enhancement has been the use of modified nucleotides such as 2'-O-methyl nucleotides, 2'-amino nucleotides, nucleotides containing 2'-O or 4'-C methylene bridges. Also, the modification of the ribonucleotide backbone connecting adjacent nucleotides has been described, mainly by the introduction of phosphorothioate modified nucleotides. It seems that enhanced stability is often inversely proportional to efficacy (Parish, 2000), and only a certain number, positions and/or combinations of modified nucleotides may result in a stable silencing compound. As this is an important hurdle within siRNA-based treatments, different studies have been published which describe certain modification patterns showing good results, examples of such include EP1527176, WO2008/050329, WO2008/104978 or WO2009/044392, although many more may be found in the literature.

The Transient Receptor Potential Vanilloid-1 (TRPV1), also called Vanilloid Receptor 1 (VR-1), is a capsaicin-responsive ligand-gated cation channel, that was first discovered in 1997 (Caterina, 1997). TRPV1 is mainly expressed on sensory neurons and serves as a molecular detector for heat, capsaicin, protons, and endovanilloids (Caterina, 2001; Montell, 2002; Baumann, 2000). Although the inventors of the present application have also found TRPV1 expression in tissues from the lacrimal gland and ciliary body.

When TRPV1 is activated by agonists such as capsaicin and other factors such as heat, acidosis, lipoxygenase products or anandamide, calcium enters the cell and pain signals are initiated. Activation of the channel induces neuropeptide release from central and peripheral sensory nerve terminals, resulting in the sensation of pain, neurogenic inflammation, and sometimes, in smooth muscle contraction and cough. As a matter of fact, recent evidence suggests a role of TRPV1 in pain, cough, asthma and urinary incontinence (Jia, 2005). In fact, TRPV1 is a known target for treatments by analgesia in response to pain stimuli. Moreover, treatments designed to reduce expression levels of TRPV1 using different technologies have also been described in WO2004/042046, or (Schubert, 2005), with a focus on the treatment of pain.

Polymodal nociceptors are the most abundant nociceptor type found in the cornea. There exists pharmacological evidence that these receptor fibers express TRPV1 receptor because they respond to capsaicin, heat and acid. Moreover, high doses of capsaicin inactivate the response of corneal polymodal nociceptors to heat and acid whereas mechanical responsiveness remains unaffected. This suggests that TRPV1 receptors present in corneal polymodal nerve endings were selectively inactivated. Therefore, it is likely that an important part of the acute nociceptive response to corneal injury and the sustained pain sensations that accompany inflammatory and irritative processes in this tissue are mediated by TRPV1 activation.

Furthermore, WO2007/045930 describes the use of TRPV1 specific siRNAs for treatment of ocular pathologies related to ocular pain and dry eye syndrome. However, the present invention provides improved products for reducing TRPV1 expression and consequent ocular discomfort. The advantage of treating these conditions with siRNA products vs traditional chemical inhibitors is that treatments based on siRNA will have a longer-lasting effect. This result is due to the fact that once the effector molecule is no longer present, the cell will have to synthesise new receptors from scratch; whereas traditional treatments would leave the levels of receptors on the cell membrane intact.

Due to current life-style, the number of people affected by ocular pathologies related to altered ocular sensitivity is quite high, and is expected to increase with aging of population. Refractive surgery and contact lens use often derive in altered corneal sensitivity and a sensation of dry eye by the patient. This is further aggravated by long working hours looking at computer screens and the use of air-conditioning systems which usually further dry the atmosphere. Also, the quantity and quality of tears decrease with age. Symptoms accompanying dry eye syndromes include itching, burning and irritation of the ocular tissues. A more severe form of dry eye occurs in patients with Sjogren's syndrome. The presence of one or different combinations of these sensations is termed ocular pain within the meaning of the present text. At present dry eye syndrome is estimated to affect over 10 million Americans.

DETAILED DESCRIPTION OF THE INVENTION

Figure 1:
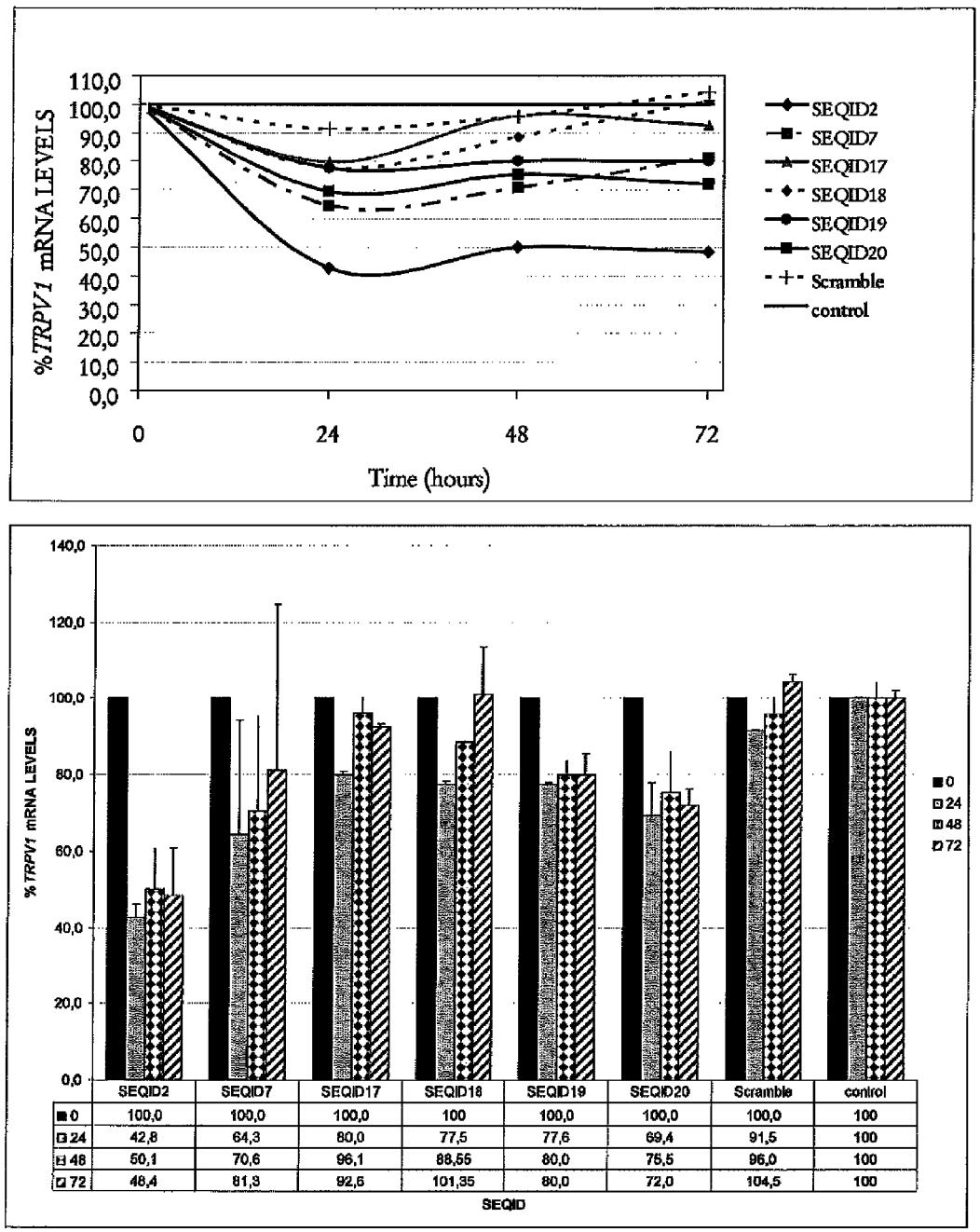
FIG. 1 is a diagram showing temporal expression profile of TRPV1, using Qrt-PCR, after transfection of HeLa cells with different siRNAs targeting TRPV1: a compound according to the present invention (SEQ ID NO: 2), a previously described compound targeting a different region (SEQ ID NO: 7), and another four siRNAs (SEQ ID NO: 17 to 20) designed to target TRPV1 and a scramble sequence used as a negative control. Two alternative representations of the same results are shown to ensure clarity.

In a first aspect, the present invention relates to the provision of an siRNA molecule wherein said molecule specifically targets SEQ ID NO: 1 and reduces expression of TRPV1 gene when introduced in a cell.

A gene is "targeted" by a siRNA according to the present invention when, for example, the siRNA molecule selectively decreases or inhibits the expression of the gene. The phrase "selectively decrease or inhibit" as used herein encompasses siRNAs that affect expression of one gene, in this case TRPV1. Alternatively, a siRNA targets a gene when the siRNA hybridizes under stringent conditions to the gene transcript, i.e. its mRNA. Capable of hybridizing "under stringent conditions" means annealing to the target mRNA region, under standard conditions, e.g., high temperature and/or low salt content which tend to disfavor hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387-389.

Nucleic acid sequences cited herein are written in a 5' to 3' direction unless indicated otherwise. The term "nucleic acid" refers to either DNA or RNA or a modified form thereof comprising the purine or pyrimidine bases present in DNA (adenine "A", cytosine "C", guanine "G", thymine "T") or in RNA (adenine "A", cytosine "C", guanine "G", uracil "U"). Interfering RNAs provided herein may comprise "T" bases, for example at 3' ends, even though "T" bases do not naturally occur in RNA. In some cases these bases may appear as "dT" to differentiate deoxyribonucleotides present in a chain of ribonucleotides.

The target sequence as defined above is described as a target DNA sequence as used for definition of transcript variants in databases used for the purposes of designing siRNAs, whereas the specific compounds to be used will be RNA sequences defined as such.

Different transcript variants corresponding to TRPV1 have been identified. GenBank Accession Numbers corresponding to four TRPV1 transcripts produced by alternative splicing are: NM_080704 (NM_080704.3, GI:117306161), NM_018727 (NM_018727.5, GI:117306160), NM_080706 (NM_080706.3, GI:117306163) and NM_080705 (NM_080705.3, GI:117306162). Furthermore, ENSEMBL (MBL-EBI/Wellcome Trust Sanger Institute) has 5 further TRPV1 transcripts published: ENST00000174621, ENST00000310522, ENST00000344161, ENST00000399752, ENST00000399756, ENST00000399759, ENST00000425167.

The present invention provides siRNAs which inhibit TRPV1 gene expression, these siRNAs being especially efficient compared to those already disclosed in the state of the art. Especially efficient meaning that they achieve higher degrees of inhibition and/or a more prolonged effect in time.

These novel siRNAs are designed against a target sequence common to all transcript variants of TRPV1 described in the preceding paragraph, and thus mediate RISC-mediated degradation of all possible mRNAs present in the cell encoding TRPV1 protein. Said preferred target region identified by the present invention is identified in SEQ ID NO: 1 (5'-AAGCG-CATCTTCTACTTCA-3').

Consequently, a siRNA according to the present invention will preferably comprise a double stranded RNA molecule, whose antisense strand will comprise an RNA sequence substantially complementary to SEQ ID NO: 1, and its sense strand will comprise an RNA sequence complementary to the antisense strand, wherein both strands are hybridised by standard base pairing between nucleotides.

Within the meaning of the present invention "substantially complementary" to a target mRNA sequence, may also be understood as "substantially identical" to said target sequence. "Identity" as is known by one of ordinary skill in the art, is the degree of sequence relatedness between nucleotide sequences as determined by matching the order and identity of nucleotides between sequences. In one embodiment the antisense strand of an siRNA having 80%, and between 80% up to 100% complementarity, for example, 85%, 90% or 95% complementarity, to the target mRNA sequence are considered substantially complementary and may be used in the present invention. The percentage of complementarity describes the percentage of contiguous nucleotides in a first nucleic acid molecule that can base pair in the Watson-Crick sense with a set of contiguous nucleotides in a second nucleic acid molecule.

As is known from the state of the art, many different structures have been proposed to achieve RNA interference. Generally these double stranded molecules are from about 19 to about 25 nucleotides in length, and include blunt-ended structures as well as those with overhangs. Overhangs have been described to be advantageous and may be present on the 5' ends or on the 3' ends of either strand as they reduce recognition by RNases and imitate Dicer's natural substrate. Some authors recommend including overhangs on both 3' ends of the molecules, whereas others consider one overhang to be sufficient. Others have described the use of blunt-ended structures with specific modification patterns (EP 1527176, WO 2008/104978, and many others).

Overhangs may be comprised of between 1 and 5 nucleotides, typically overhangs are made up of dinucleotides. Classical molecules used in the field, comprise a 19 nucleotide double stranded molecule which further comprises 3' dinucleotide overhangs preferably comprising deoxynucleotides as taught in initial studies by Tuschl (WO02/44321). These overhangs are said to further enhance resistance to nuclease (RNase) degradation. Later, Kim et al 2005 describe that 21-mer products (containing dinucleotide overhangs) are necessary for loading onto RISC. Further, Bramsen et al. 2009 describe the introduction of possible destabilizing modifications to the overhangs to further increase silencing efficiency.

As such, a preferred embodiment of the present invention refers to siRNA molecules targeting SEQ ID NO: 1 which comprise at least one overhang.

Another alternative embodiment of the present invention provides blunt-ended molecules.

Further, a preferred embodiment of the present invention relates to an siRNA comprising or consisting of a 19 nucleotide double-stranded structure targeting SEQ ID NO: 1. Surprisingly, said 19 nucleotide double-stranded RNAs have proven to be more resistant to degradation than previously described products with 21 nucleotides and 3' overhangs as may be seen in FIG. 5.

A particular embodiment of the present invention relates to a 19 nucleotide double-stranded blunt-ended siRNA targeted against SEQ ID NO: 1. In a further particular embodiment this compound is identified as SEQ ID NO: 2 (5'-AAGCG-CAUCUUCUACUUCA-3'). In a further preferred embodiment, the antisense strand of this siRNA is at least 80%, preferably at least 90%, complementary to SEQ ID NO: 1.

Furthermore, as described in the section termed background of the art, an important issue with siRNA molecules is their instability in biological fluids due to the ubiquitous nature of RNAses. Consequently, the use of many different chemical modifications to nucleotides has been described with the purpose of enhancing compound stability.

Another inherent problem of siRNA molecules is their immunogenicity, whereby siRNAs have been found to induce unspecific activation of the innate immune system, including up-regulation of certain cytokines, e.g. type I and/or type II interferon as well as IL-12, IL-6 and/or TNF-alpha production. The origin of these effects is thought to be activation of Toll-like receptors such as TLR7, TLR8 and/or TLR3 by siRNA.

Both of these effects, recognition by RNases and immunogenicity, have also been described to be sequence-dependent.

Some of the chemical modifications which enhance compound stability by decreasing susceptibility to RNAses are also able to reduce induction of immune recognition of subsequent response. However, insertion of chemically modified nucleotides in a siRNA may also result in decreased silencing efficacy as described in the previous section, and hence must be approached with caution.

Consequently, in a preferred embodiment of the present invention, the siRNA further comprises at least one nucleotide with a chemical modification.

Preferred chemical modifications which enhance stability and reduce immunogenic effects include 2'-O-methyl nucleotides, 2'-fluoro nucleotides 2'-amino nucleotides, 2'-deoxy nucleotides, nucleotides containing 2'-O or 4'-C methylene bridges. Also, the modification of the ribonucleotide backbone connecting adjacent nucleotides by the introduction of phosphorothioate modified nucleotides. A further preferred chemical modification within the meaning of the present invention relates to the substitution of uracyl ribonucleotides with deoxythymidine (deoxyribonucleotides). In another preferred embodiment of the present invention, the at least one chemically modified nucleotide is on the sense strand, on the antisense strand or on both strands of the siRNA.

Accordingly, in one embodiment, the siRNA is selected from SEQ ID. NO. 3, 4, 5, 6, 8, 9, 10, 11, 12, 13, 14, 15 or 16.

siRNA molecules as described above may be delivered to the cell interior in their native structure using methods known in the art. For example, when studying in vitro gene silencing, these compounds are administered using standard transfection reagents. To achieve effects in vivo these compounds may also be administered naked or using delivery enhancing agents such as for example liposomes, conjugation with a specific moiety, etc. although many different alternatives are known in the art, and are used differently depending on the desired target site within the body.

Alternatively, siRNA molecules of the invention can be expressed within cells from eukaryotic promoters. Recombinant vectors capable of expressing the siRNA molecules can be delivered and persist in target cells. Alternatively, vectors can be used that provide for transient expression of nucleic acid molecules. Such vectors can be repeatedly administered as necessary. Once expressed, the siRNA molecule interacts with the target mRNA and generates an RNA interfering response. The siRNA molecules produced in this manner are often termed shRNA (short hairpin RNA), as their sense and antisense strands are joined by a small loop of nucleotides.

Delivery of siRNA molecule expressing vectors can be systemic, such as by intravenous or intra-muscular administration, by administration to target cells ex-planted from a subject followed by reintroduction into the subject, or by any other means that would allow for introduction into the desired target cell.

A further aspect of the invention relates to the use of smRNA targeting SEQ ID NO. 1 in the preparation of a medicament for use in a method of treatment of an eye condition characterised by increased expression and/or activity of TRPV1. The method comprises inhibiting expression of TRPV1 in a patient. The term inhibition is used to indicate a decrease or downregulation of expression or activity. Preferably, the eye condition is ocular pain. In one embodiment, the eye condition is selected from the group comprising ocular discomfort and altered sensitivity of the cornea following refractive surgery, use of contact lenses, dry eye syndrome, Sjogren's syndrome, and other eye pathologies.

Therapeutic treatment with siRNAs directed against TRPV1 mRNA is expected to be beneficial over small molecule topical ocular drops by increasing the length of time that effect is observed, thereby allowing less frequent dosing and greater patient compliance. This is especially important in cases such as dry eye syndrome and altered corneal sensitivity as they are often chronic conditions.

Bearing in mind the preparation of such a medicament, the siRNA of the present invention may be formulated. Preferably, the compositions and formulations of said siRNAs may be administered topically to the organ of interest. In an even more preferred embodiment they may be formulated for topical administration to the eye, preferably to the corneal surface of the eye. Application to the corneal surface may, for example be in the form of eyedrops, a gel, lotion, cream or ocular inserts. Other administration forms to the eye may include injection into the eye.

A further preferred embodiment of the present invention relates to an siRNA specifically targeting SEQ ID NO: 1 as described in the preceding paragraphs, for use as a medicament for the treatment of an eye condition characterised by increased expression and/or activity of TRPV1. As described above, it may be an siRNA comprising or consisting of a 19 nucleotide double-stranded structure targeting SEQ ID NO: 1. This siRNA may be blunt-ended. Preferably, the siRNA is SEQ ID NO: 2. Other siRNA for use according to the invention may be selected from SEQ ID. NO. 3, 4, 5, 6, 8, 9, 10, 11, 12, 13, 14, 15 or 16.

Within the context of the present invention, to "specifically target" a sequence the siRNA of the invention must comprise at least the same seed sequence. Thus, any sequence according to the invention that specifically targets SEQ ID No. 1 must be identical in positions 2-8 of the antisense strand.

Notwithstanding the above, the siRNAs of the present invention may be used to silence TRPV1 expression in tissues other than the eye. Consequently, said siRNAs should be formulated accordingly.

For example, a siRNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

A siRNA molecule of the invention may be complexed with membrane disruptive agents and/or a cationic lipid or helper lipid molecule.

Delivery systems which may be used with the invention include, for example, aqueous and non aqueous gels, creams, multiple emulsions, microemulsions, liposomes, ointments, aqueous and non aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize.

The formulations or siRNA of the invention and described herein can be administered in unit dosage formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agents. The pharmaceutical compositions or siRNA of the invention and described herein can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

As such, a further preferred embodiment of the present invention regards a pharmaceutical composition wherein said composition comprises at least an siRNA targeting SEQ ID NO: 1, as has been described in the preceding paragraphs.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

The invention is further described in the following non-limiting examples.

EXAMPLES

In vitro Analysis

In order to find a particularly effective target sequence for siRNAs to silence TRPV1 (which obtain important inhibition of gene expression), six different siRNAs were tested. These siRNAs are described as SEQ ID NO: 2, SEQ ID NO: 7 and SEQ ID NO: 17 to 20.

SEQ ID NO: 2 is an siRNA targeting SEQ ID NO: 1 according to the present invention having the following sequence:

```
Sense:
5'-AAGCGCAUCUUCUACUUCA-3'

Antisense:
5'-UGAAGUAGAAGAUGCGCUU-3'
```

SEQ ID NO: 7 (5'-UCGCCACGACAUGCUCUUGdTdT-3') corresponds to a classical siRNA molecule (21 nucleotides in length containing 3' overhangs made of deoxythymidine) previously described in WO 2007/045930 to effectively target TRPV1 and reduce ocular response to capsaicin stimuli. SEQ ID NO: 17 to 19 correspond to siRNAs designed against TRPV1 according to different algorithms available in the art such as those described by Reynolds et al. 2004 or Ui-Tei et al 2004, and others. SEQ ID NO: 20 is a commercially available siRNA supplied by Ambion and designed against TRPV1.

SEQ ID NO: 17
Sense:
5'-CGCAUCUUCUACUUCAACU-3'

Antisense:
5'-AGUUGAAGUAGAAGAUGCG-3'

SEQ ID NO: 18
Sense:
5'-GCGCAUCUUCUACUUCAAC-3'

Antisense:
5'-GUUGAAGUAGAAGAUGCGC-3'

SEQ ID NO: 19
Sense:
5'-AAAGCCAUGCUCAACCUGC-3'

Antisense:
5'-GCAGGUUGAGCAUGGCUUU-3'

SEQ ID NO: 20
Sense:
5'-UGAUCGCAGGAGUAUCUUUdTdT-3'

Antisense:
5'-AAAGAUACUCCUGCGAUCAdTdT-3'

As a model to test effectiveness of the above described siRNA, HeLa (human cervix adenocarcinoma) cell cultures were used. HeLa cells were transfected with 100 nM of different compounds and Lipofectamine 2000 as a transfectant agent. All transfections were done following standard manufacturer's conditions. In the same transfection a different scramble siRNA was used as control. Cell pellets were collected at 24, 48, and 72 hours to evaluate possible variations in protein levels and processed by real-time PCR. In order to quantify the results obtained by real-time Qrt-PCR, we used the Comparative Threshold Method.

As results show (FIG. 1), an siRNA directed against target sequence SEQ ID NO: 1, is much more efficient in terms of TRPV1 gene silencing than previously described siRNA products directed against a different region of the same gene. Moreover this effect is sustained in time, as at 72 hours post-transfection there is still significant downregulation of mRNA levels. This duration of the effect is unpredictable and is sequence specific.

With the objective of providing further improved products, different chemical modifications were introduced on the above product, according to the description below:

SEQ ID NO: 3
Sense:
5'-AAGCGCAUCUUCUACUUCA-3'

Antisense:
5'-UGAAGUAGAAGAUGCGCUU-3',

SEQ ID NO: 4
Sense:
5'-AAGCGCAUCUUCUACUUCA-3'

Antisense:
5'-UGAAGUAGAAGAUGCGCUU-3',

SEQ ID NO: 8
Sense:
5'-AAGCGCAUCUUCUACUUCA-3'

Antisense:
5'-UGAAGUAGAAGAUGCGCUU-3',

SEQ ID NO: 9
Sense:
5'-AAGCGCAUCUUCUACUUCA-3'

Antisense:
5'-UGAAGUAGAAGAUGCGCUU-3',

SEQ ID NO: 10
Sense:
5'-AAGCGCAUCUUCUACUUCA-3'

Antisense:
5'-UGAAGUAGAAGAUGCGCUU-3',

SEQ ID NO: 11
Sense:
5'-AAGCGCAUCUUCUACUUCA-3'

Antisense:
5'-UGAAGUAGAAGAUGCGCUU-3',

Wherein the underline represents bases comprising a 2'-Omethyl group.

SEQ ID NO: 5
Sense:
5'-AAGCGCAdTCdTdTCdTACdTdTCA-3'

Antisense:
5'-UGAAGUAGAAGAUGCGCUU-3',

SEQ ID NO: 6
Sense:
5'-AAGCGCAdTCdTdTCdTACdTCA-3'

Antisense:
5'-dTGAAGdTAGAAGAdTGCGCdTdT-3',

SEQ ID NO: 12
Sense:
5'-AAGCGCAdTCUdTCdTACdTdTCA-3'

Antisense:
5'-UGAAGUAGAAGAUGCGCUU-3',

SEQ ID NO: 13
Sense:
5'-AAGCGCAdTCUdTCdTACUdTCA-3'

Antisense:
5'-UGAAGUAGAAGAUGCGCUU-3',

SEQ ID NO: 14
Sense:
5'-AAGCGCAdTCUUCdTACUdTCA-3'

Antisense:
5'-UGAAGUAGAAGAUGCGCUU-3',

SEQ ID NO: 15
Sense:
5'-AAGCGCAdTCUUCUACUdTCA-3'

Antisense:
5'-UGAAGUAGAAGAUGCGCUU-3',

-continued

SEQ ID NO: 16
Sense:
5'-AAGCGCAdTCUUCUACUdTCA-3'

Antisense:
5'-UGAAGdTAGAAGAdTGCGCUU-3',

Wherein some or all uracyl nucleotides have been substituted for deoxythymidine nucleotides.

These compounds were tested in immunogenicity assays along with SEQ ID NO: 2 (the same compound without any modified nucleotides). Results showed that all these compounds significantly reduced induction of an immune response in peripheral blood mononuclear cells. Moreover, most compounds induced a response which was at its highest levels, as low as that produced by siRNAs which have advanced through human clinical trials (bevasiranib and Sirna-027) which were included in the assays as a control.

As varying degrees of modification can alter gene silencing ability of siRNAs, these compounds were further tested for their RNA interfering capacity by transfection into HeLa cells, and resulting TRPV1 mRNA levels were measured according to the method described in preceding paragraphs.

Figure 2:
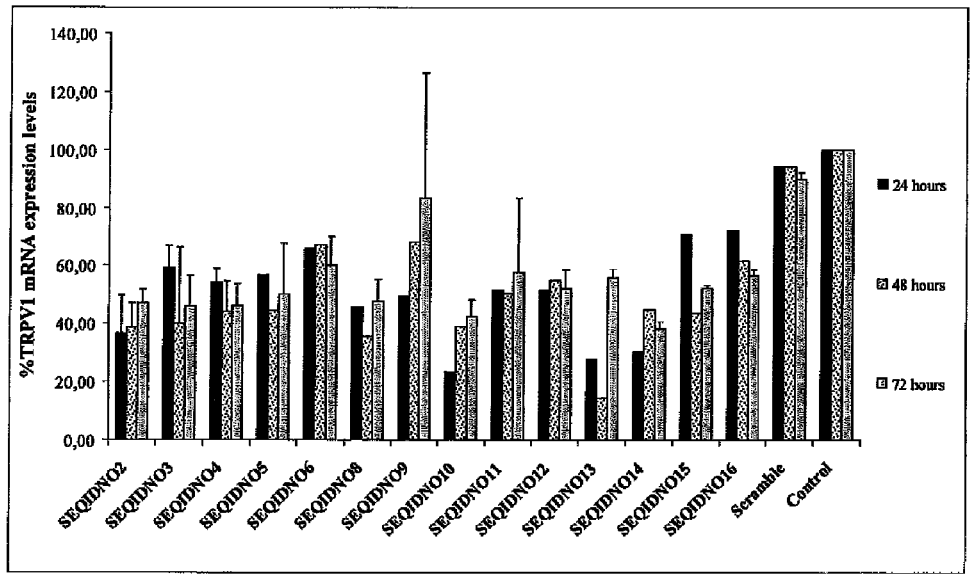
FIG. 2 is a diagram showing temporal expression profile of TRPV1, using Qrt-PCR, after transfection of HeLa cells with different siRNAs of the present invention: SEQ ID NO: 2 to SEQ ID NO: 6, and SEQ ID NO: 8 to SEQ ID NO: 16, and a scramble sequence used as a negative control.

As may be seen in FIG. 2, all compounds retain the ability to efficiently decrease TRPV1 mRNA levels in varying degrees.

Figure 5:
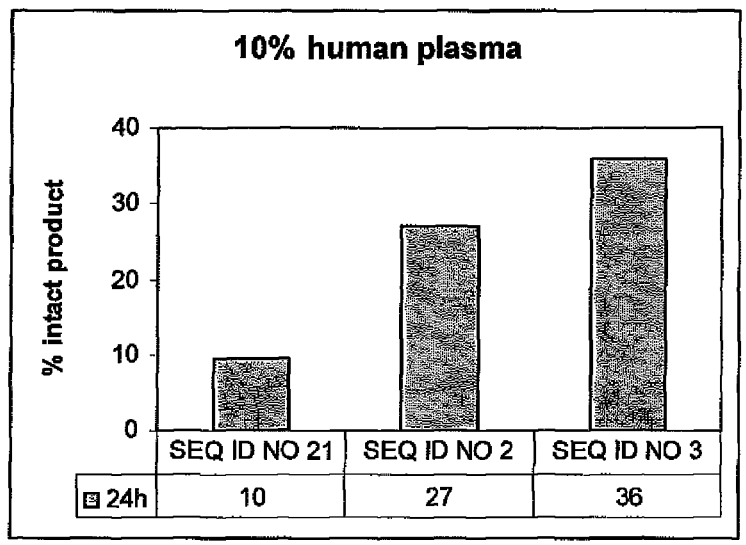
FIG. 5 is a graph showing the amount of intact product (%) remaining after being exposed to 10% plasma for 24 hours.

A further unexpected beneficial effect derived from the above described compounds is their enhanced resistance to degradation by RNases as may be seen in FIG. 5.

For these experiments, compounds were suspended in 10% human plasma in PBS at a final concentration of 2 µM and incubated for 24 hours at 37° C. Samples were then analysed using HPLC-UV and the amount of remaining intact product is determined. As may be observed in FIG. 5, the 19 nucleotide double-stranded compound of SEQ ID NO: 2 (without any chemical modification) is almost 3 times more resistant to degradation than previously described SEQ ID NO: 21: 5'-CAAGAUCGCACAGGAGAGCdTdT-3' (also described in WO 2007045930) which comprises 3' overhangs. This effect is further enhanced for compound of SEQ ID NO: 3, which includes some chemically modified nucleotides as described in preceding paragraphs.

In vivo Analysis

Animal models of dry eye and ocular pain often make use of rabbits, in this case New Zealand White rabbits. To this end, a further advantage of the siRNAs of the present invention is that the target sequence, SEQ ID NO: 1, is a highly conserved region of the TRPV1 gene, throughout different animal sequences. In fact, this sequence is identical between human and rabbit, making this animal model especially suitable for the study of said diseases.

The experiment described below was performed using a standard model of ocular pain known to an expert in the field (Gonzalez et al. 1993). Briefly, pain was induced using instillation of 30 µl of a solution of 1% capsaicin (a known agonist of TRPV1) to the eye using an appropriate micropipette. Due to ethical considerations, animals to be treated with capsaicin had previously received a dose of capsazepine 5 mM, a known capsaicin antagonist, or 40 µl of a solution containing the compound to be tested. Therefore analgesic effect is measured in comparison to capsazepine as a reference treatment.

Test and reference items were instilled once a day from Day 1 to Day 3 and twice a day on Day 4 (pace out of 60 min) in the right eyes. At Day 4, 15 minutes following the last instillation, corneal pain was induced in the right eye of the animals by a single instillation of capsaicin 1%. The contralateral eye was instilled with PBS throughout the study and served as control.

To measure response to pain, palpebral opening was measured. It is considered that the eye is closed in response to pain, and as pain sensations subside the palpebral opening will increase back to normal levels. The palpebral opening was measured before treatment (baseline), just before pain induction and then 1, 5, 10, 15, 20, 25, 30, minutes after pain induction.

Figure 3:
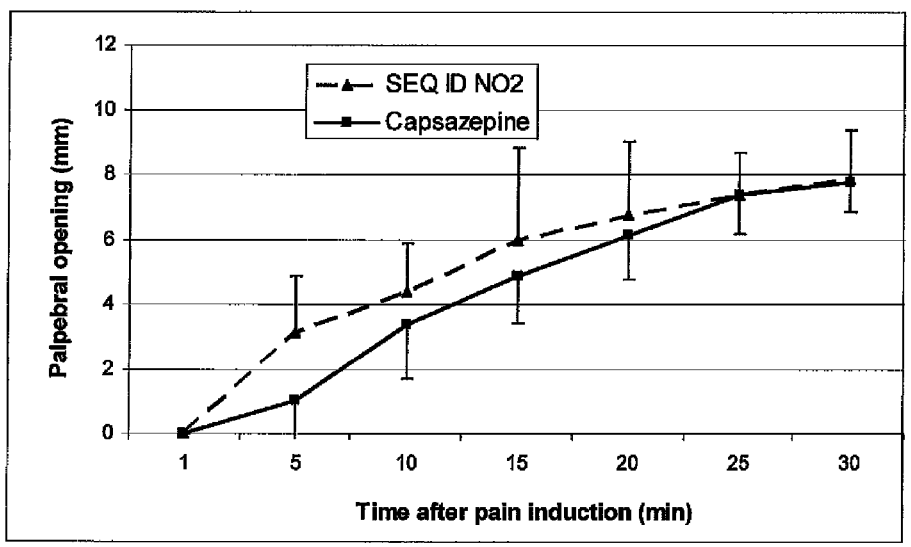
FIG. 3 shows a timeline with the palpebral opening measured in mm of the eyes from rabbits treated with a compound of the present invention (SEQ ID NO: 2) in comparison to capsazepine, an accepted specific analgesic for TRPV1 dependent pain, after stimulation with capsaicin.
Figure 4:
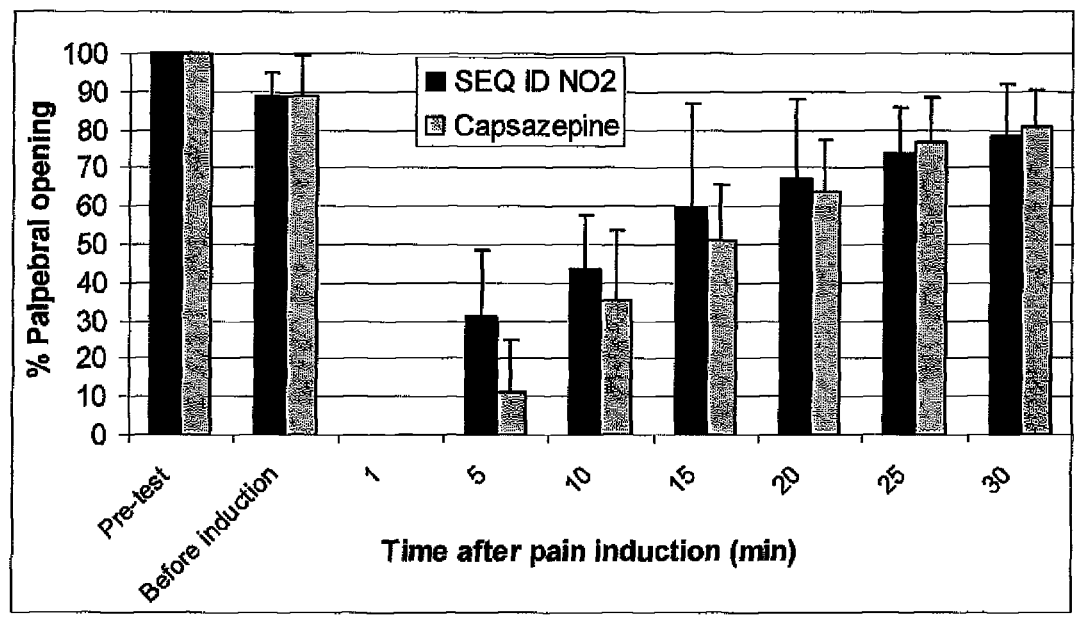
FIG. 4 is a graph showing the ratio (%) with respect to pre-test values, of the palpebral opening after pain induction with capsaicin, resulting from treatment with a compound of the present invention (SEQ ID NO: 2) and capsazepine.

As may be seen from FIGS. 3 and 4, a compound according to the present invention was tested, specifically the compound of SEQ ID NO: 2, and was observed to induce a higher analgesic effect than capsazepine (eye recovery as measured by degree of palpebral opening). Therefore this compound has proven to be an effective therapeutic treatment for ocular discomfort.

Furthermore, another in vivo experiment was performed in which the compounds of the present invention (SEQ ID NO: 2, SEQ ID NO: 4 and SEQ ID NO: 5) were administered to rabbits eyes, along with SEQ ID NO: 21, previously described in WO 2007045930. In this case, rabbits (6 animals per treatment group) received a daily administration of the compound during 3 consecutive days. On the third day, two hours after the last instillation, animals were sacrificed. Ocular tissues from these rabbits were recovered and presence of TRPV1 specific mRNA was analyzed using RT-PCR. The following table shows the levels of TRPV1 gene silencing achieved in a given tissue expressed as a ratio of the % of inhibition achieved with reference compound SEQ ID NO: 21.

|  | SEQ ID NO: 2 | SEQ ID NO: 4 | SEQ ID NO: 5 |
| --- | --- | --- | --- |
| Lacrimal gland | 3.06 | 3.15 | 1.92 |
| Ciliary body | 6.54 | 2.48 | 3.57 |

As is clear from these results, the compounds of the present invention are much more effective when silencing TRPV1 gene expression in ocular tissues than previously described compounds.

The higher efficacy together with the longer lasting effect of the compounds of the invention, should provide advantageous dose regimes, as allowing more time between doses would significantly improve patients' quality of life.

REFERENCES

Baumann T K & Martenson M E. (2000). "Extracellular protons both increase the activity and reduce the conductance of capsaicin-gated channels." *J Neurosci* 20:RC80.

Caterina et al. (1997). "The capsaicin receptor: a heat-activated ion channel in the pain pathway." *Nature* 389(6653): 816-24.

Caterina et al. (2001). "The vanilloid receptor: a molecular gateway to the pain pathway." *Annu Rev Neurosci.* 24:487-517.

Cerutti, L., N. Mian, et al. (2000). "Domains in gene silencing and cell differentiation proteins: the novel PAZ domain and redefinition of the Piwi domain." *Trends Biochem Sci* 25(10): 481-2.

Collins, R. E. and X. Cheng (2005). "Structural domains in RNAi." *FEBS Lett* 579(26): 5841-9.

Doench, J. G. Sharp, P. A. "specificity of microRNA target selection in translational repression" Genes Dev. 18, 504-511; 2004

Elbashir, S. M., W. Lendeckel, et al. (2001). "RNA interference is mediated by 21- and 22-nucleotide RNAs." *Genes Dev* 15(2): 188-200.

Fire, A., S. Xu, et al. (1998). "Potent and specific genetic interference by double-stranded RNA in *Caenorhabditis elegans*." *Nature* 391(6669): 806-11.

Gonzalez, G. G., Garcia, P. et al. (1993). "Reduction of capsacin-induced ocular pain and neurogenic inflammation by calcium antagonists." *Invest Ophthalmol Vis Sci* 34(12): 3329-3335.

Hutvagner, G. and P. D. Zamore (2002). "A microRNA in a multiple-turnover RNAi enzyme complex." *Science* 297 (5589): 2056-60.

Jia et al. (2005). "TRPV1 receptor: a target for the treatment of pain, cough, airway disease and urinary incontinence." *Drug News Perspect* 18(3):165-71.

Lewis, B. P., Shih I. Et al. "prediction of mammalian micro RNA targets" Cell 115:787-798; 2003

Liu, J., M. A. Carmell, et al. (2004). "Argonaute2 is the catalytic engine of mammalian RNAi." *Science* 305(5689): 1437-41.

Ma, J. B., Y. R. Yuan, et al. (2005). "Structural basis for 5'-end-specific recognition of guide RNA by the *A. fulgidus* Piwi protein." *Nature* 434(7033): 666-70.

Montell et al. (2002). "Short hairpin RNAs (shRNAs) induce sequence-specific silencing in mammalian cells." *Genes Dev* 16(8):948-58.

Nykanen, A., B. Haley, et al. (2001). "ATP requirements and small interfering RNA structure in the RNA interference pathway." *Cell* 107(3): 309-21.

Orban, T. I. and E. Izaurralde (2005). "Decay of mRNAs targeted by RISC requires XRN1, the Ski complex, and the exosome." *Rna* 11(4): 459-69.

Parrish, S., J. Fleenor, et al. (2000). "Functional anatomy of a dsRNA trigger: differential requirement for the two trigger strands in RNA interference." *Mol Cell* 6(5): 1077-87.

Rand, T. A., S. Petersen, et al. (2005). "Argonaute2 cleaves the anti-guide strand of siRNA during RISC activation." *Cell* 123(4): 621-9.

Reynolds, A., Leake, D., et al. (2004). "Rational siRNA design for RNA interference" *Nat Biotechnol* 22(3):326-30.

Schubert, S. et al. (2005). "Local RNA target structure influences siRNA efficacy: systematic analysis of intentionally designed binding regions." *J Mol Biol* 348:883-893.

Song, J. J., S. K. Smith, et al. (2004). "Crystal structure of Argonaute and its implications for RISC slicer activity." *Science* 305(5689): 1434-7.

Ui-Tei, K., Naito, Y., et al. (2004). "Guidelines for the selection of highly effective siRNA sequences for mammalian and chick RNA interference." *Nucleic Acids Res* 32(3): 936-48.

---

The invention claimed is:

1. A method of treating an eye condition characterized by increased expression and/or activity of Transient Receptor Potential Vanilloid 1 (TRPV1), comprising:
topically administering to the corneal surface of the eye of a patient in need thereof an effective amount of a short interfering ribonucleic acid (siRNA) molecule comprising a double stranded RNA portion consisting of a 19-nucleotide double stranded RNA in which one strand of the double stranded portion consists of the nucleotide sequence as set forth in SEQ ID NO: 2;
wherein the siRNA specifically targets the nucleotide sequence as set forth in SEQ ID NO: 1 in ocular tissue of the patient, and wherein expression and/or activity of TRPV1 nucleic acid is decreased or downregulated following topical administration of the siRNA to the corneal surface of the patient's eye.

2. The method according to claim 1, wherein the eye condition is ocular pain.

3. The method according to claim 1, wherein the eye condition is altered sensitivity following refractive surgery.

4. The method according to claim 1, wherein the siRNA is blunt-ended.

5. The method according to claim 1, wherein at least one nucleotide of the siRNA molecule comprises a chemical modification.

6. The method according to claim 5, wherein the chemical modification of the at least one nucleotide comprises 2'-O-methylation.

7. The method according to claim 5, wherein the chemical modification is on the sense strand, the antisense strand, or on both strands.

8. The method according to claim 5, wherein the nucleotide sequence of the siRNA comprising the chemical modification is selected from the group consisting of SEQ ID NO: 3 to SEQ ID NO: 6, and SEQ ID NO: 8 to SEQ ID NO: 16.

9. The method according to claim 5, wherein the chemical modification of the at least one nucleotide comprises substitution of uracyl ribose nucleotides with deoxythymidine nucleotides.

10. The method according to claim 1, wherein the eye condition is ocular discomfort or corneal sensitivity following use of contact lenses.

11. The method according to claim 1, wherein the eye condition is dry eye syndrome.

12. The method according to claim 1, wherein the eye condition is Sjogren's syndrome.

13. The method according to claim 1, wherein the siRNA has a 3' dinucleotide overhang.

14. The method according to claim 13, wherein the dinucleotide overhang contains thymidine nucleotides.

* * * * *